United States Patent
Cauwet-Martin et al.

(10) Patent No.: US 6,503,494 B1
(45) Date of Patent: Jan. 7, 2003

(54) COMPOSITION COMPRISING SILICONE POLYMER CONTAINING NON-SILICONE BACKBONE AND AT LEAST ONE THICKENING POLYMER OR COPOLYMER OF (METH) CRYLAMIDE OR OF A (METH) ACRYLAMIDE DERIVATIVE

(75) Inventors: Daniele Cauwet-Martin, Paris (FR); Claude Dubief, Le Chesnay (FR); Christine Dupuis, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/542,293

(22) Filed: Apr. 4, 2000

Related U.S. Application Data

(63) Continuation of application No. 08/983,343, filed as application No. PCT/FR96/01438 on Sep. 16, 1996, now Pat. No. 6,056,945.

(30) Foreign Application Priority Data

Sep. 29, 1995 (FR) .............................. 95 11485

(51) Int. Cl.$^7$ ................................. A61K 7/06
(52) U.S. Cl. ................ 424/70.1; 424/70.11; 424/70.12; 424/70.122; 424/70.121; 424/70.15; 424/70.17
(58) Field of Search ............ 424/70.11, 70.12, 424/70.122, 70.121, 70.15, 70.17, 70.1

(56) References Cited

U.S. PATENT DOCUMENTS

| | | | |
|---|---|---|---|
| 5,061,481 A | 10/1991 | Suzuki et al. ............ 424/63 |
| 5,219,560 A | 6/1993 | Suzuki et al. ............ 424/63 |
| 5,229,435 A | 7/1993 | Sakai et al. ............. 523/105 |
| 5,480,634 A | 1/1996 | Hayama et al. .......... 424/70.12 |
| 5,643,581 A | 7/1997 | Mougin et al. ........... 424/401 |
| 6,024,946 A | * 2/2000 | Dubief et al. ........... 424/70 |

FOREIGN PATENT DOCUMENTS

| | | |
|---|---|---|
| EP | 0 412 704 | 2/1991 |
| EP | 0 492 657 | 7/1992 |
| EP | 0 524 612 | 1/1993 |
| EP | 0 636 361 | 2/1995 |
| EP | 524612 | * 5/1995 |
| FR | 2 709 955 | 3/1995 |
| JP | 2132141 | 5/1990 |
| JP | 2250812 | 10/1990 |
| JP | 2258709 | 10/1990 |
| JP | 2279617 | 11/1990 |
| JP | 3008432 | 1/1991 |
| WO | 91/15186 | 10/1991 |
| WO | WO 92/21316 | * 12/1992 |
| WO | 95/00108 | 1/1995 |
| WO | 95/00108 | * 5/1995 |

OTHER PUBLICATIONS

English Language Derwent Abstract of EP 0 636 361. Feb. 1995.
English Language Derwent Abstract of FR 2 709 955. Mar. 1995.

* cited by examiner

Primary Examiner—Thurman K. Page
Assistant Examiner—Lakshmi Channavajjala
(74) Attorney, Agent, or Firm—Finnegan, Henderson, Farabow, Garrett & Dunner, L.L.P.

(57) ABSTRACT

The present invention relates to a cosmetic or dermatological composition for treating keratin substances, in particular human hair, comprising a grafted silicone polymer with a non-silicone organic skeleton with at least one monomer containing at least one polysiloxane and at least one crosslinked or non-crosslinked thickening polymer or copolymer of methacrylamide or a methacrylamide derivative.

52 Claims, No Drawings

COMPOSITION COMPRISING SILICONE POLYMER CONTAINING NON-SILICONE BACKBONE AND AT LEAST ONE THICKENING POLYMER OR COPOLYMER OF (METH) CRYLAMIDE OR OF A (METH) ACRYLAMIDE DERIVATIVE

This is a continuation of application Ser. No. 08/983,343, filed Dec. 30, 1997, now U.S. Pat. No. 6,056,945 which is a U.S. National Phase application of PCT/FR96/01438, filed Sep. 16, 1996, all of which are incorporated herein by reference.

The present invention relates to a cosmetic or dermatological composition for treating keratin substances, in particular human hair, this composition comprising at least one grafted silicone polymer comprising a polysiloxane portion and a portion consisting of a non-silicone organic chain, one of the two portions constituting the main chain of the polymer, the other being grafted onto the said main chain, and at least one thickening polymer or copolymer of (meth)acrylamide or of a (meth)acrylamide derivative, as well as to its applications.

Polymers of the grafted silicone polymer type comprising a polysiloxane portion and a portion consisting of a non-silicone organic chain, one of the two portions constituting the main chain of the polymer, the other being grafted onto the said main chain, are known for their hairstyling properties. They are particularly advantageous in haircare cosmetics since they give the hair hold. However, after they have been applied to the hair, their cosmetic properties are still unsatisfactory. It is observed that after applying these polymers, the hair has a coarse and crisp feel resulting from non-continuous distribution of the polymer along the hair fibres.

The Applicant has found, surprisingly, that the use of a crosslinked or non-crosslinked thickening polymer or copolymer of (meth)acrylamide or of a (meth)acrylamide derivative in haircare compositions containing a polymer of the grafted silicone polymer type comprising a polysiloxane portion and a portion consisting of a non-silicone organic chain, one of the two portions constituting the main chain of the polymer, the other being grafted onto the said main chain, makes it possible to improve, after it has been applied, the deposition of the grafted silicone polymer along the keratin fibres and to improve their cosmetic properties, in particular as regards their feel, while at the same time retaining the styling properties of the grafted silicone polymer.

The composition according to the invention is thus essentially characterized in that it contains, in a cosmetically or dermatologically acceptable medium, at least one grafted silicone polymer comprising a polysiloxane portion and a portion consisting of a non-silicone organic chain, one of the two portions constituting the main chain of the polymer, the other being grafted onto the said main chain, and at least one crosslinked or non-crosslinked thickening polymer or copolymer of (meth)acrylamide or of a (meth)acrylamide derivative.

The grafted silicone polymers according to the invention are preferably chosen from polymers having a non-silicone organic skeleton grafted with monomers containing a polysiloxane, polymers having a polysiloxane skeleton grafted with non-silicone organic monomers and mixtures thereof.

In the following text, in accordance with what is generally accepted, the term silicone or polysiloxane is understood to denote any organosilicon polymer or oligomer having a linear or cyclic, branched or crosslinked structure of variable molecular weight, obtained by polymerization and/or polycondensation of suitably functionalized silanes, and consisting essentially of a repetition of main units in which the silicon atoms are linked together by oxygen atoms (siloxane bonding $\equiv$Si—O—Si$\equiv$), optionally substituted hydrocarbon radicals being linked directly via a carbon atom to the said silicon atoms. The most common hydrocarbon radicals are alkyl radicals, especially $C_1$–$C_{10}$ alkyl radicals, and in particular methyl, fluoroalkyl radicals, aryl radicals and in particular phenyl, and alkenyl radicals and in particular vinyl; other types of radicals which can be linked, either directly or via a hydrocarbon radical, to the siloxane chain are, especially, hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, substituted or unsubstituted amine groups, amide groups, acyloxy radicals or acyloxyalkyl radicals, hydroxyalkylamino or aminoalkyl radicals, quaternary ammonium groups, amphoteric or betaine groups, anionic groups such as carboxylates, thioglycolates, sulphosuccinates, thiosulphates, phosphates and sulphates, needless to say this list not being limiting in any way (so-called "organomodified" silicones).

In the following text, in accordance with what is generally accepted, the expression "polysiloxane macromer" is understood to refer to any monomer containing a polysiloxane-type polymer chain in its structure.

The polymers containing a non-silicone organic skeleton grafted with monomers containing a polysiloxane, in accordance with the present invention, consist of an organic main chain formed from organic monomers containing no silicone, on which is grafted, inside the said chain and optionally on at least one of its ends, at least one polysiloxane macromer.

The non-silicone organic monomers constituting the main chain of the grafted silicone polymer can be chosen from monomers containing ethylenic unsaturation which are polymerizable via a radical route, monomers which are polymerizable by polycondensation, such as those forming polyamides, polyesters or polyurethanes, and monomers which involve ring opening, such as those of the oxazoline or caprolactone type.

The polymers containing a non-silicone organic skeleton grafted with monomers containing a polysiloxane, in accordance with the present invention, can be obtained according to any means known to those skilled in the art, in particular by reaction between (i) a starting polysiloxane macromer which is correctly functionalized on the polysiloxane chain and (ii) one or more non-silicone organic compounds, themselves correctly functionalized with a function which is capable of reacting with the functional group(s) borne by the said silicone, forming a covalent bond; a classic example of such a reaction is the radical reaction between a vinyl group borne on one of the ends of the silicone with a double bond of a monomer containing ethylenic unsaturation in the main chain.

The polymers containing a non-silicone organic skeleton grafted with monomers containing a polysiloxane, in accordance with the invention, are more preferably chosen from those described in U.S. Pat. Nos. 4,693,935, 4,728,571 and 4,972,037 and patent applications EP-A-0,412,704, EP-A-0,412,707, EP-A-0,640,105 and WO 95/00578. These are copolymers obtained by radical polymerization starting with monomers containing ethylenic unsaturation and silicone macromers having a terminal vinyl group, or alternatively copolymers obtained by reaction of a polyolefin comprising functionalized groups and a polysiloxane macromer having a terminal function which is reacted with the said functionalized groups.

One particular family of silicone polymers which is suitable for carrying out the present invention consists of silicone grafted copolymers comprising:

a) from 0 to 98% by weight of at least one lipophilic monomer (A) of low lipophilic polarity containing ethylenic unsaturation, which is polymerizable via a radical route;

b) from 0 to 98% by weight of at least one polar hydrophilic monomer (B) containing ethylenic unsaturation, which is copolymerizable with the (A)-type monomer(s);

c) from 0.01 to 50% by weight of at least one polysiloxane macromer (C) of general formula:

where:

X denotes a vinyl group which is copolymerizable with the monomers (A) and (B);

Y denotes a divalent bonding group;

R denotes a hydrogen, a $C_1$–$C_6$ alkyl or alkoxy or a $C_6$–$C_{12}$ aryl;

Z denotes a monovalent polysiloxane unit having a number-average molecular weight of at least 500;

n is 0 or 1 and m is an integer ranging from 1 to 3;

the percentages being calculated relative to the total weight of the monomers (A), (B) and (C).

These polymers are described, along with processes for their preparation, in U.S. Pat. Nos. 4,693,935, 4,728,571 and 4,972,037 and in patent applications EP-A-0,412,704, EP-A-0,412,707 and EP-A-0,640,105. They have a number-average molecular weight preferably ranging from 10,000 to 2,000,000 and preferably a glass transition temperature Tg or a crystalline melting point Tm of at least −20° C.

As examples of lipophilic monomers (A), mention may be made of acrylic or methacrylic acid esters of $C_1$–$C_{18}$ alcohols; styrene; polystyrene macromers; vinyl acetate; vinyl propionate; α-methylstyrene; tert-butylstyrene; butadiene; cyclohexadiene; ethylene; propylene; vinyltoluene; acrylic or methacrylic acid esters of a 1,1-dihydroperfluoroalkanol or of homologues thereof; acrylic or methacrylic acid esters of ω-hydridofluoroalkanols; acrylic or methacrylic acid esters of a fluoroalkylsulphoamido alcohol; acrylic or methacrylic acid esters of a fluoroalkyl alcohol; acrylic or methacrylic acid esters of a fluoroether alcohol; or mixtures thereof.

The preferred monomers (A) are chosen from the group consisting of n-butyl methacrylate, isobutyl methacrylate, tert-butyl acrylate, tert-butyl methacrylate, 2-ethylhexyl methacrylate, methyl methacrylate, 2-(N-methylperfluorooctanesulphonamido)ethyl acrylate and 2-(N-butylperfluorooctanesulphonamido)ethyl acrylate, and mixtures thereof.

As examples of polar monomers (B), mention may be made of acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride and semiesters thereof, hydroxyalkyl (meth)acrylates, diallyldimethylammonium chloride, vinylpyrrolidone, vinyl ethers, maleimides, vinylpyridine, vinylimidazole, heterocyclic vinyl polar compounds, styrene sulphonate, allyl alcohol, vinyl alcohol and vinyl caprolactam, or mixtures thereof. The preferred monomers (B) are chosen from the group consisting of acrylic acid, N,N-dimethylacrylamide, dimethylaminoethyl methacrylate, quaternized dimethylaminoethyl methacrylate and vinylpyrrolidone, and mixtures thereof.

The preferred polysiloxane macromers (C) of formula (I) are chosen from those corresponding to the general formula (II) below:

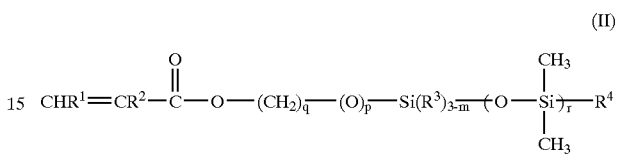

in which:

$R^1$ is hydrogen or —COOH (preferably hydrogen);

$R^2$ is hydrogen, methyl or —$CH_2COOH$ (preferably methyl);

$R^3$ is $C_1$–$C_6$ alkyl, alkoxy, or alkylamino, $C_6$–$C_{12}$ aryl or hydroxyl (preferably methyl); $R^4$ is $C_1$–$C_6$ alkyl, alkoxy or alkylamino, $C_6$–$C_{12}$ aryl or hydroxyl (preferably methyl);

q is an integer from 2 to 6 (preferably 3);

p is 0 or 1;

r is an integer from 5 to 700;

m is an integer from 1 to 3 (preferably 1).

The polysiloxane macromers of formula:

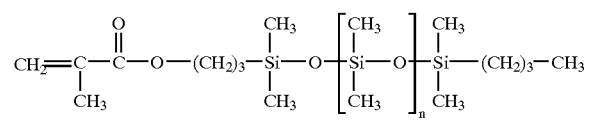

with n being an integer ranging from 5 to 700, are more particularly used.

One particular embodiment of the invention consists in using a copolymer which can be obtained by radical polymerization starting with the monomer mixture consisting of:

a) 60% by weight of tert-butyl acrylate;

b) 20% by weight of acrylic acid;

c) 20% by weight of silicone macromer of formula:

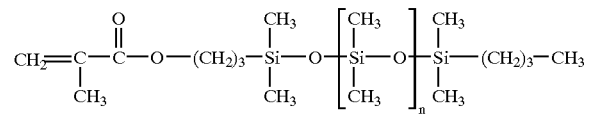

with n being an integer ranging from 5 to 700; the weight percentages being calculated relative to the total weight of the monomers.

Another particular embodiment of the invention consists in using a copolymer which can be obtained by radical polymerization starting with the monomer mixture consisting of:

a) 80% by weight of tert-butyl acrylate;
b) 20% by weight of silicone macromer of formula:

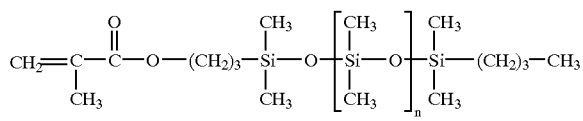

with n being an integer ranging from 5 to 700; the weight percentages being calculated relative to the total weight of the monomers.

Another particular family of silicone polymers, which is suitable for carrying out the present invention, consists of silicone grafted copolymers which can be obtained by reactive extrusion of a polysiloxane macromer having a terminal reactive function, with a polyolefin-type polymer containing reactive groups which can react with the terminal function of the polysiloxane macromer in order to form a covalent bond allowing grafting of the silicone to the main chain of the polyolefin.

These polymers are described, along with a process for their preparation, in patent application WO 95/00578.

The reactive polyolefins are preferably chosen from polyethylenes or polymers of ethylene-derived monomers such as propylene, styrene, alkylstyrene, butylene, butadiene, (meth)acrylates, vinyl esters or equivalents, containing reactive functions which can react with the terminal function of the polysiloxane macromer. They are chosen more particularly from copolymers of ethylene or of ethylene derivatives and of monomers chosen from those containing a carboxylic function, such as (meth)acrylic acid; those containing an acid anhydride function such as maleic anhydride; those containing an acid chloride function such as (meth)acryloyl chloride; those containing an ester function such as (meth) acrylic acid esters; those containing an isocyanate function.

The silicone macromers are preferably chosen from polysiloxanes containing a functionalized group, at the end of the polysiloxane chain or close to the end of the said chain, chosen from the group consisting of alcohols, thiols, epoxy groups and primary and secondary amines, and more particularly from those corresponding to the general formula (III):

$$T-(CH_2)_s-Si-[-(OSiR^5R^6)_t-R^7]_y.$$ (III)

in which T is chosen from the group consisting of $NH_2$, NHR', an epoxy, OH, or SH function; $R^5$, $R^6$, $R^7$ and R', independently denote a $C_1$–$C_6$ alkyl, phenyl, benzyl, $C_6$–$C_{12}$ alkylphenyl or hydrogen; s is a number from 2 to 100; t is a number from 0 to 1000 and y is a number from 1 to 3. They have a number-average molecular weight preferably ranging from 5000 to 300,000, more preferably from 8000 to 200,000 and more particularly from 9000 to 40,000.

According to the present invention, the grafted silicone polymer(s) containing a polysiloxane skeleton grafted with non-silicone organic monomers comprise a silicone (or polysiloxane $(\equiv Si-O-)_n$) main chain on which is grafted, inside the said chain as well as, optionally, on at least one of its ends, at least one organic group containing no silicone.

The polymers containing a polysiloxane skeleton grafted with non-silicone organic monomers, according to the invention, can be existing commercial products or alternatively can be obtained according to any means known to those skilled in the art, in particular by reaction between (i) a starting silicone which is correctly functionalized on one or more of these silicon atoms, and (ii) a non-silicone organic compound which is itself correctly functionalized with a function which is capable of reacting with the functional group(s) borne by the said silicone, forming a covalent bond; a classic example of such a reaction is the hydrosilylation reaction between $\equiv Si-H$ groups and vinyl groups $CH_2=CH-$, or alternatively the reaction between thio functional groups $-SH$ with these same vinyl groups.

Examples of polymers with a polysiloxane skeleton grafted containing non-silicone organic monomers which are suitable for carrying out the present invention, as well as their specific mode of preparation, are described in particular in patent application s EP-A-0,582,152, WO 93/23009 and WO 95/03776, the teachings of which are included in their entirety in the present description by way of non-limiting references.

According to a particularly preferred embodiment of the present invention, the silicone polymer containing a polysiloxane skeleton grafted with non-silicone organic monomers, which is used comprises the result of the radical copolymerization between, on the one hand, at least one non-silicone anionic organic monomer having ethylenic unsaturation and/or a non-silicone hydrophobic organic monomer having ethylenic unsaturation, and, on the other hand, a silicone having in its chain at least one functional group capable of reacting with the said ethylenic unsaturations of the said non-silicone monomers, forming a covalent bond, in particular thio functional groups.

According to the present invention, the said anionic monomers containing ethylenic unsaturation are preferably chosen, alone or as a mixture, from linear or branched, unsaturated carboxylic acids, optionally partially or totally neutralized in the form of a salt, it being possible for this (these) carboxylic acid(s) to be, more particularly, acrylic acid, methacrylic acid, maleic acid, maleic anhydride, itaconic acid, fumaric acid and crotonic acid The suitable salts are, in particular, alkali metal salts, alkaline-earth metal salts and ammonium salts. It will likewise be noted that, in the final grafted silicone polymer, the organic group of anionic nature which comprises the result of the radical (homo) polymerization of at least one anionic monomer of unsaturated carboxylic acid type can, after reaction, be post-neutralized with a base (sodium hydroxide, aqueous ammonia, etc) in order to bring it into the form of a salt.

According to the present invention, the hydrophobic monomers containing ethylenic unsaturation are preferably chosen, alone or as a mixture, from acrylic acid esters of alkanols and/or methacrylic acid esters of alkanols. The alkanols are preferably $C_1$–$C_{18}$ and more particularly $C_1$–$C_{12}$. The preferred monomers are chosen from the group consisting of isooctyl (meth)acrylate, isononyl (meth) acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth) acrylate, tridecyl (meth)acrylate and stearyl (meth)acrylate, or mixtures thereof.

One family of silicone polymers containing a polysiloxane skeleton grafted with non-silicone organic monomers which is particularly suitable for carrying out the present invention consists of silicone polymers containing in their structure the unit of formula (IV) below:

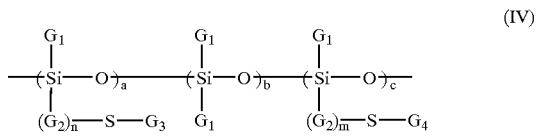

(IV)

in which the radicals $G_1$, which may be identical or different, represent hydrogen or a $C_1$–$C_{10}$ alkyl radical or alternatively a phenyl radical; the radicals $G_2$, which may be identical or different, represent a $C_1$–$C_{10}$ alkylene group; $G_3$ represents a polymer residue resulting from the (homo)polymerization of at least one anionic monomer containing ethylenic unsaturation; $G_4$ represents a polymer residue resulting from the (homo)polymerization of at least one hydrophobic monomer containing ethylenic unsaturation; m and n are equal to 0 or 1; a is an integer ranging from 0 to 50; b is an integer which may be between 10 and 350, c is an integer ranging from 0 to 50; with the proviso that one of the parameters a and c is other than 0.

Preferably, the unit of formula (IV) above has at least one, and even more preferably all, of the following characteristics:

the radicals $G_1$ denote an alkyl radical, preferably the methyl radical;

n is non-zero and the radicals $G_2$ represent a divalent $C_1$–$C_3$ radical, preferably a propylene radical;

$G_3$ represents a polymeric radical resulting from the (homo)polymerization of at least one monomer of the carboxylic acid type containing ethylenic unsaturation, preferably acrylic acid and/or methacrylic acid;

$G_4$ represents a polymeric radical resulting from the (homo)polymerization of at least one monomer of the $C_1$–$C_{10}$ alkyl (meth)acrylate type, preferably isobutyl or methyl (meth)acrylate.

Examples of grafted silicone polymers corresponding to formula (IV) are, in particular, polydimethylsiloxanes (PDMS) on which are grafted, via a thiopropylene-type connecting chain, mixed polymer units of the poly(meth) acrylic acid type and of the polymethyl (meth)acrylate type.

Other examples of silicone polymers corresponding to formula (IV) are, in particular, polydimethylsiloxanes (PDMS) on which are grafted, via a thiopropylene-type connecting chain, polymer units of the polyisobutyl (meth) acrylate type.

Preferably, the number-average molecular mass of the silicone polymers containing a polysiloxane skeleton grafted with non-silicone organic monomers, of the invention, ranges approximately from 10,000 to 1,000,000 and even more preferably approximately from 10,000 to 100,000.

The silicone grafted polymers of the invention are preferably used in an amount ranging from 0.01 to 20% by weight relative to the total weight of the composition. More preferably, this amount ranges from 0.1 to 15% by weight and even more preferably from 0.5 to 10% by weight.

As preferred thickening polymers or copolymers of (meth)acrylamide or of a (meth)acrylamide derivative which are suitable for the compositions of the invention, mention may be made of the following polymers:

(i) crosslinked copolymers of 2-acrylamido-2-methylpropanesulphonic acid which are partially or totally neutralized (with a base such as sodium hydroxide, potassium hydroxide or an amine) and of acrylamide, such as the product described in Example 1 of document EP-A-503,853;

(ii) crosslinked or non-crosslinked copolymers of ammonium acrylate and of (meth)acrylamide, such as the product sold under the name Bozepol C Nouveau or the product PAS 5193 sold by the company Hoechst (these are described and prepared in documents FR 2,416,723, U.S. Pat. Nos. 2,798,053 and 2,923,692);

(iii) crosslinked or non-crosslinked copolymers of dimethylaminoethyl methacrylate quaternized with methyl chloride and of (meth)acrylamide, such as the product Salcare SC92 sold by Allied Colloids or the product PAS 5194 sold by Hoechst (these are described in document EP-A-395,282);

(iv) mixtures thereof.

The polymers or copolymers of (meth)acrylamide or of a (meth)acrylamide derivative according to the invention are used in an amount ranging from 0.01 to 20% by weight relative to the total weight of the composition. More preferably, this amount ranges from 0.1 to 15% by weight and even more preferably from 0.5 to 10% by weight.

The cosmetically or dermatologically acceptable medium preferably consists of water or a mixture of water and cosmetically acceptable solvents such as monoalcohols, polyalcohols, glycol ethers or fatty acid esters, which can be used alone or as a mixture.

Mention may be made more particularly of lower alcohols such as ethanol and ispropanol, polyalcohols such as diethylene glycol, glycol ethers, glycol alkyl ethers or diethylene glycol alkyl ethers.

The grafted silicone polymers according to the invention can be dissolved in the said cosmetically acceptable medium or used in the form of an aqueous dispersion of particles.

The composition of the invention can also contain at least one additive chosen from thickeners, fatty acid esters, fatty acid esters of glycerol, silicones, surfactants, fragrances, preserving agents, sunscreens, proteins, vitamins, polymers, plant, animal, mineral or synthetic oils or any other additive conventionally used in the cosmetic field.

These additives are present in the composition according to the invention in proportions which can range from 0 to 20% by weight relative to the total weight of the composition. The precise amount of each additive depends on its nature and is determined readily by those skilled in the art.

Needless to say, a person skilled in the art will take care to select the optional compound(s) to be added to the composition according to the invention such that the advantageous properties intrinsically associated with the composition in accordance with the invention are not, or are not substantially, adversely affected by the addition envisaged.

The compositions according to the invention can be in the form of a gel, a milk, a cream, a relatively thickened lotion or a mousse.

These compositions are more particularly hairsetting lotions, blow-drying lotions, fixing compositions (lacquers) and styling compositions. The lotions can be packaged in various forms, in particular in vapourizers, pump-dispenser bottles or in aerosol containers in order to ensure application of the composition in vapourized form or in the form of a mousse. Such packaging forms are indicated, for example, when it is desired to obtain a spray, a lacquer or a mousse for fixing or treating the hair.

The compositions can also be shampoos, rinse-out or leave-in compositions, to be applied before or after shampooing, dyeing, bleaching, permanent-waving or straightening the hair.

When the composition according to the invention is packaged in aerosol form in order to obtain a lacquer or an aerosol mousse, it comprises at least one propellant which can be chosen from volatile hydrocarbons such as n-butane, propane, isobutane, pentane, a chloro and/or fluoro hydrocarbon, and mixtures thereof. Carbon dioxide, nitrous oxide, dimethyl ether, nitrogen or air, which is compressed, and mixtures thereof, can also be used as propellant.

Another subject of the invention is a non-therapeutic process for treating keratin substances such as the hair, which consists in applying a composition as defined above to the hair and then optionally in rinsing with water.

The invention will now be illustrated more fully with the aid of the examples which follow, which should not be considered as limiting it to the embodiments described.

EXAMPLES

Example 1

Conditioner

Grafted silicone polymer of formula (IV) of polymethyl/methylsiloxane structure containing 3-propylthio polyisobutyl methacrylate groups 2 g AM Crosslinked acrylamide /trimethylethylammonium methacrylate chloride 42/58 copolymer as a 50% dispersion in oil, sold under the name Salcare SC 92 by Allied Colloids 2 g AM Fragrance, preserving agent qs Water qs 100 g 100 g pH adjusted to 7 with NaOH

Example 2

Conditioner

Grafted silicone polymer of formula (IV) of polymethyl/methylsiloxane structure containing 3-propylthio polymethacyrlic acid groups and 3-propylthio polymethyl methacrylate groups 1 g AM Crosslinked acrylamide/2-acrylamidomethylpropanesulphonic acid copolymer in the form of the sodium salt, as a 40% inverted emulsion in an isoparaffin/water mixture, such as the product described in Example 1 of document EP-A-503,853 1 g AM Polydimethylsiloxane 350 cst 1 g Fragrance, preserving agent qs Water qs 100 g pH adjusted to 6 with NaOH.

What is claimed is:

1. A cosmetic or dermatological composition comprising, in a cosmetically or dermatologically acceptable medium,
   (a) at least one grafted silicone polymer having a non-silicone organic skeleton grafted with at least one monomer containing at least one polysiloxane and
   (b) at least one crosslinked or non-crosslinked thickening polymer or copolymer of (meth)acrylamide or of a (meth)acrylamide derivative,
   wherein the polymer of (a) and the polymer or copolymer of (b) are not identical, and
   wherein the polymer or copolymer of (b) is chosen from
       (i) partially and totally neutralized, crosslinked copolymers of 2-acrylamido-2-methylpropanesulphonic acid,
       (ii) crosslinked and non-crosslinked copolymers of ammonium acrylate and (meth)acrylamide; and
       (iii) crosslinked and non-crosslinked copolymers of dimethylaminoethyl methacrylate quaternized with methyl chloride and of (meth)acrylamide.

2. A cosmetic or dermatological composition according to claim 1, wherein said composition is a treatment composition for a keratin substance.

3. A cosmetic or dermatological composition according to claim 2, wherein said keratin substance is human hair.

4. A cosmetic or dermatological composition according to claim 1, wherein said at least one grafted silicone polymer contains a non-silicone organic skeleton, comprising an organic main chain formed from at least one organic monomer containing no silicone, and further wherein on said organic main chain is grafted, inside said main chain and optionally on at least one end of said main chain, at least one polysiloxane macromer.

5. A cosmetic or dermatological composition according to claim 4, wherein said at least one organic monomer containing no silicone constituting the main chain of said at least one grafted silicone polymer is selected from monomers containing ethylenic unsaturation which are polymerizable via a radical route, monomers which are polymerizable by polycondensation and monomers which involve ring opening.

6. A cosmetic or dermatological composition according to claim 1, wherein said at least one silicone grafted copolymer comprises:
   a) up to 98% by weight of at least one lipophilic monomer (A) of low polarity containing ethylenic unsaturation of low polarity, which is polymerizable via a radical route;
   b) up to 98% by weight of at least one polar hydrophilic monomer (B) containing ethylenic unsaturation, which is copolymerizable with said (A) monomer(s);
   c) from 0.01 to 50% by weight of at least one polysiloxane macromer (C) of formula:

$$X(Y)_n Si(R)_{3-m} Z_m \qquad (I)$$

in which:

X denotes a vinyl group which is copolymerizable with the monomers (A) and (B);

Y denotes a divalent bonding group;

R denotes a hydrogen, a $C_1$–$C_6$ alkyl or alkoxy or a $C_6$–$C_{12}$ aryl;

Z denotes a monovalent polysiloxane unit having a number-average molecular weight of at least 500;

n is 0 or 1; and m is an integer ranging from 1 to 3;

wherein the percentages are calculated relative to the total weight of the monomers (A), (B) and (C) and wherein the sum of a) and b) cannot constitute 0% by weight relative to the total weight of the monomers.

7. A cosmetic or dermatological composition according to claim 6, wherein said at least one lipophilic monomer (A) is selected from acrylic and methacrylic acid esters of $C_1$–$C_8$ alcohols; styrene; polystyrene macromers; vinyl acetate; vinyl propionate; α-methylstyrene; tert-butylstyrene; butadiene; cyclohexadiene; ethylene; propylene; vinyltoluene; acrylic and methacrylic acid esters of a 1,1-dihydroperfluoroalkanol and of homologues thereof; acrylic and methacrylic acid esters of ω-hydridofluoroalkanols; acrylic and methacrylic acid esters of a fluoroalkylsulphoamido alcohols; acrylic and methacrylic acid esters of fluoroalkyl alcohols; and acrylic and methacrylic acid esters of fluoroether alcohols.

8. A cosmetic or dermatological composition according to claim 7, wherein said at least one lipophilic monomer (A) is selected from n-butyl methacrylate, isobutyl methacrylate, tert-butyl acrylate, tert-butyl methacrylate, 2-ethylhexyl methacrylate, methyl methacrylate, 2-(N-methylperfluorooctanesulphonamido)ethyl acrylate and 2-(butylperfluorooctanesulphonamido)ethyl acrylate.

9. A cosmetic or dermatological composition according to claim 8, wherein said at least one polar hydrophilic monomer (B) is selected from acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride and demiesters thereof, hydroxyalkyl (meth)acrylates, diallyldimethylammonium chloride, vinylpyrrolidone, vinyl ethers, maleimides, vinylpyridine, vinylimidazole, heterocyclic vinyl polar compounds, styrene sulphonate, allyl alcohol, vinyl alcohol and vinyl caprolactam.

10. A cosmetic or dermatological composition according to claim 9, wherein said at least one polar hydrophilic monomer (B) is selected from acrylic acid, N,N-dimethylacrylamide, dimethylaminoethyl methacrylate, quaternized dimethylaminoethyl methacrylate and vinylpyrrolidone.

11. A cosmetic or dermatological composition according to claim 6, wherein said at least one polysiloxane macromer (C) has the formula (II):

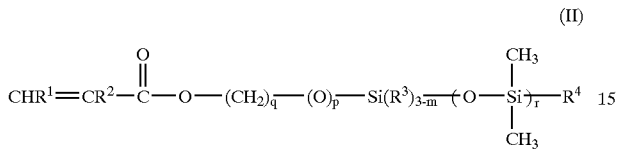

(II)

in which:

$R^1$ is hydrogen or —COOH;

$R^2$ is hydrogen, methyl or —CH$_2$COOH;

$R^3$ is $C_1$–$C_6$ alkyl, alkoxy, or alkylamino, $C_6$–$C_{12}$ aryl or hydroxyl;

$R^4$ is $C_1$–$C_6$ alkyl, alkoxy or alkylamino, $C_6$–$C_{12}$ aryl or hydroxyl;

q is an integer from 2 to 6;

p is 0 or 1;

r is an integer from 5 to 700;

m is an integer from 1 to 3.

12. A cosmetic or dermatological composition according to claim 11, wherein $R^1$ is hydrogen.

13. A cosmetic or dermatological composition according to claim 11, wherein $R^2$ is methyl.

14. A cosmetic or dermatological composition according to claim 11, wherein $R^3$ is methyl.

15. A cosmetic or dermatological composition according to claim 11, wherein $R^4$ is methyl.

16. A cosmetic or dermatological composition according to claim 11, wherein q is 3.

17. A cosmetic or dermatological composition according to claim 12, wherein m is 1.

18. A cosmetic or dermatological composition according to claim 6, wherein said at least one polysiloxane macromer (C) is selected from compounds corresponding to the following formula:

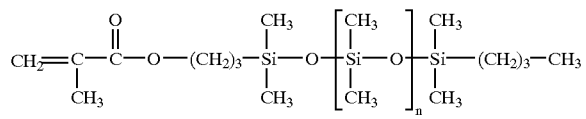

in which n is an integer ranging from 5 to 700.

19. A cosmetic or dermatological composition according to claim 1, wherein said at least one grafted silicone polymer contains at least one copolymer which can be obtained by radical polymerization of a monomer mixture comprising:

a) 60% by weight of tert-butyl acrylate;

b) 20% by weight of acrylic acid; and c) 20% by weight of silicone macromer of formula:

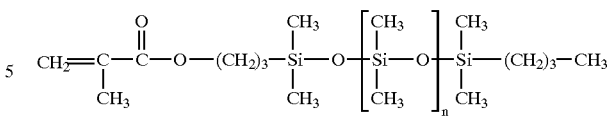

in which
n is integer ranging from 5 to 700;
wherein the weight percentages are calculated relative to the total weight of said monomer mixture.

20. A cosmetic or dermatological composition according to claim 1, wherein said at least one grafted silicone polymer contains at least one copolymer which can be obtained by radical polymerization of a monomer mixture comprising:

a) 80% by weight of tert-butyl acrylate; and b) 20% by weight of silicone macromer of formula:

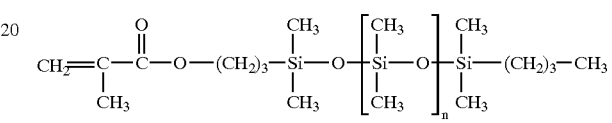

in which:
n is an integer ranging from 5 to 700;
wherein the weight percentages are calculated relative to the total weight of said monomer mixture.

21. A cosmetic or dermatological composition according to claim 1, wherein said polymers containing a non-silicone organic skeleton grafted with at least one monomer containing at least one polysiloxane have a number-average molecular weight ranging from 10,000 to 2,000,000 and a glass transition temperature Tg or a crystalline melting point Tm of at least −20° C.

22. A cosmetic or dermatological composition according to claim 1, wherein said at least one grafted silicone polymer is a polymer containing a non-silicone organic skeleton grafted with at least one monomer containing at least one polysiloxane, and further wherein said at least one polymer is obtained by reactive extrusion of a polysiloxane macromer having a terminal reactive function, with a polyolefin polymer containing reactive groups which can react with the reactive terminal function of said at least one polysiloxane macromer to form a covalent bond resulting in a grafting of the silicone to said polyolefin polymer, said polyolefin polymer forming the skeleton of said polymers.

23. A cosmetic or dermatological composition according to claim 22, wherein said polyolefin polymer is selected from polyethylenes and polymers of ethylene-derived monomers containing reactive functions which can react with the terminal function of the polysiloxane macromer.

24. A cosmetic or dermatological composition according to claim 22, wherein said polyolefin polymer is selected from copolymers of (a) ethylene and/or of ethylene derivatives and of (b) monomers selected from monomers containing a carboxylic function; monomers containing an acid anhydride function; monomers containing an acid chloride function; monomers containing an ester function; and monomers containing an isocyanate function.

25. A cosmetic or dermatological composition according to claim 4, wherein said at least one polysiloxane macromer is a polysiloxane containing a functionalized group at the end of the polysiloxane chain or close to the end of said chain, wherein said functionalized group is selected from alcohols, thiols, epoxy groups and primary and secondary amines.

26. A cosmetic or dermatological composition according to claim 4, wherein said at least one polysiloxane macromer is a polysiloxane corresponding to formula (III):

$$T-(CH_2)_s-Si-[-(OSiR^5R^6)_t-R^7]_y \quad (III)$$

in which

T is selected from $NH_2$, NHR', an epoxy, OH, and SH functions;

$R^5$, $R^6$, $R^7$ and R' each independently denotes a $C_1$–$C_6$ alkyl, phenyl, benzyl, $C_6$–$C_{12}$ alkylphenyl or hydrogen;

s is a number ranging from 2 to 100;

t is a number ranging from 0 to 1000 and y is a number ranging from 1 to 3.

27. A cosmetic or dermatological composition according to claim 26, wherein said polysiloxane corresponding to formula (III) has a number-average molecular weight ranging from 5000 to 300,000.

28. A cosmetic or dermatological composition according to claim 27, wherein said polysiloxane corresponding to formula (III) has a number-average molecular weight ranging from 8000 to 200,000.

29. A cosmetic or dermatological composition according to claim 28, wherein said polysiloxane corresponding to formula (III) has a number-average molecular weight ranging from 9000 to 40,000.

30. A cosmetic or dermatological composition according to claim 1, wherein said composition comprises at least one grafted silicone polymer containing a polysiloxane main chain grafted with at least one non-silicone organic monomer, wherein on said polysiloxane main chain is grafted, inside said main chain and optionally on at least one of its ends, said at least one non-silicone organic monomer.

31. A cosmetic or dermatological composition according to claim 30, wherein said at least one grafted silicone polymer comprises, on the main silicone chain, at least one organic group of anionic nature obtained by the radical (homo)polymerization of at least one anionic monomer of unsaturated carboxylic acid partially or totally neutralized in the form of a salt.

32. A cosmetic or dermatological composition according to claim 30, wherein said at least one grafted silicone polymer is selected from silicone polymers containing in their structure at least one unit of formula (IV):

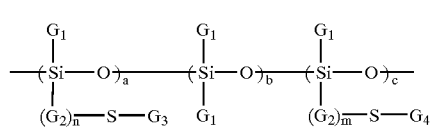

in which:

the radicals $G_1$ each independently represent hydrogen, a $C_1$–$C_{10}$ alkyl radical or a phenyl radical;

the radicals $G_2$ each independently represent a divalent $C_1$–$C_{10}$ alkylene group;

$G_3$ represents a polymer residue resulting from the (homo)polymerization of at least one anionic monomer containing ethylenic unsaturation;

$G_4$ represents a polymer residue resulting from the (homo)polymerization of at least one hydrophobic monomer containing ethylenic unsaturation;

m and n are equal to 0 or 1;

a is an integer ranging from 0 to 50;

b is an integer ranging from 10 to 350; and c is an integer ranging from 0 to 50;

with the proviso that one of a and c is not 0.

33. A cosmetic or dermatological composition according to claim 32, wherein said at least one unit of formula (IV) has at least one of the following characteristics:

the radicals $G_1$ denote a $C_1$–$C_{10}$ alkyl radical;

n is 1;

the radicals $G_2$ represent a divalent $C_2$–$C_3$ radical;

$G_3$ represents a polymeric residue resulting from the (homo)polymerization of at least one carboxylic acid monomer containing ethylenic unsaturation; and $G_4$ represents a polymeric residue resulting from the (homo)polymerization of at least one $C_1$–$C_{10}$ alkyl (meth)acrylate monomer.

34. A cosmetic or dermatological composition according to claim 32, wherein said at least one unit of formula (IV) simultaneously has the following characteristics:

the radicals $G_1$ denote a methyl radical;

n is 1;

the radicals $G_2$ represent a propylene radical;

$G_3$ represents a polymeric residue resulting from the (homo)polymerization of at least one monomer selected from acrylic acid and methacrylic acid; and $G_4$ represents a polymeric residue resulting from the (homo)polymerization of at least one monomer selected from isobutyl and methyl (meth)acrylate monomers.

35. A cosmetic or dermatological composition according to claim 30, wherein said at least one grafted silicone polymer has a number-average molecular mass ranging from 10,000 to 1,000,000.

36. A cosmetic or dermatological composition according to claim 30, wherein said at least one grafted silicone polymer has a number-average molecular mass ranging from 10,000 to 100,000.

37. A cosmetic or dermatological composition according to claim 1, wherein said at least one grafted silicone polymer is present in a concentration ranging from 0.01 to 20% by weight relative to the total weight of the composition.

38. A cosmetic or dermatological composition according to claim 37, wherein said at least one grafted silicone polymer is present in a concentration ranging from 0.1 to 15% by weight relative to the total weight of the composition.

39. A cosmetic or dermatological composition according to claim 38, wherein said at least one grafted silicone polymer is present in a concentration ranging from 0.5 to 10% by weight relative to the total weight of the composition.

40. A cosmetic or dermatological composition according to claim 1, wherein said at least one thickening polymer or copolymer of (meth)acrylamide or of a (meth)acrylamide derivative is present in a concentration ranging from 0.01 to 20% by weight relative to the total weight of the composition.

41. A cosmetic or dermatological composition according to claim 40, wherein said at least one thickening polymer or copolymer of (meth)acrylamide or of a (meth)acrylamide derivative is present in a concentration ranging from 0.1 to 15% by weight relative to the total weight of the composition.

42. A cosmetic or dermatological composition according to claim 41, wherein said at least one thickening polymer or copolymer of (meth)acrylamide or of a (meth)acrylamide derivative is present in a concentration ranging from 0.5 to 10% by weight relative to the total weight of the composition.

43. A cosmetic or dermatological composition according to claim 1, wherein said composition further comprises at least one additive selected from the group consisting of thickeners with no fatty chain, fatty acid esters, fatty acid esters of glycerol, silicones, surfactants, fragrances, preserving agents, sunscreens, proteins, vitamins, different polymers, plant, animal, mineral and synthetic oils and any other suitable cosmetic additive.

44. A cosmetic or dermatological composition according to claim 1, wherein said cosmetically or dermatologically acceptable medium comprises water or a mixture of water and at least one cosmetically acceptable solvent.

45. A cosmetic or dermatological composition according to claim 44, wherein said at least one cosmetically acceptable solvent is selected from monoalcohols, polyalcohols, glycol ethers and fatty acid esters.

46. A cosmetic or dermatological composition according to claim 1, wherein said at least one grafted silicone polymer is dissolved in the cosmetically or dermatologically acceptable medium or is in the form of an aqueous dispersion of particles.

47. A cosmetic or dermatological composition according to claim 1, wherein said composition is in the form of a gel, a milk, a cream, a thickened lotion or a mousse.

48. A cosmetic or dermatological composition according to claim 1, wherein said composition is a hair product.

49. A cosmetic or dermatological composition according to claim 48, wherein said hair product is selected from shampoos and rinse-out and leave-in hair products, to be applied before or after shampooing, dyeing, bleaching, permanent-waving or straightening the hair.

50. A cosmetic or dermatological composition according to claim 1, wherein said composition is packaged in the form of a vaporizer, a pump-dispenser bottle or an aerosol container.

51. A non-therapeutic process comprising applying a composition according to claim 1 to a keratin substance and then optionally rinsing with water.

52. A non-therapeutic process according to claim 51, wherein said keratin substance is human hair.

* * * * *

UNITED STATES PATENT AND TRADEMARK OFFICE
CERTIFICATE OF CORRECTION

PATENT NO. : 6,503,494 B1  Page 1 of 1
DATED : January 7, 2003
INVENTOR(S) : Daniele Cauwet et al.

It is certified that error appears in the above-identified patent and that said Letters Patent is hereby corrected as shown below:

Column 10,
Line 38, "$C_1$-$C_8$" should read -- $C_1$-$C_{18}$ --.

Column 12,
Line 54, "claim 22," should read -- claim 23, --.

Column 14,
Line 11, "$C_2$-$C_3$" should read -- $C_1$-$C_3$ --.

Signed and Sealed this

Twenty-ninth Day of July, 2003

JAMES E. ROGAN
*Director of the United States Patent and Trademark Office*